United States Patent
Nord et al.

(10) Patent No.: US 7,809,107 B2
(45) Date of Patent: Oct. 5, 2010

(54) METHOD FOR CONTROLLING MODULATION STRENGTH IN RADIATION THERAPY

(75) Inventors: Janne Ilmari Nord, Espoo (FI); Jarkko Yrjänä Peltola, Tuusula (FI)

(73) Assignee: Varian Medical Systems International AG, Zug (CH)

( * ) Notice: Subject to any disclaimer, the term of this patent is extended or adjusted under 35 U.S.C. 154(b) by 1 day.

(21) Appl. No.: 12/165,479

(22) Filed: Jun. 30, 2008

(65) Prior Publication Data

US 2009/0326615 A1     Dec. 31, 2009

(51) Int. Cl.
*A61N 5/10* (2006.01)
(52) U.S. Cl. .......................................... 378/65
(58) Field of Classification Search ................ 378/65
See application file for complete search history.

(56) References Cited

U.S. PATENT DOCUMENTS 7,162,008 B2 * 1/2007 Earl et al. ................. 378/65
7,180,980 B2 * 2/2007 Nguyen ...................... 378/65

\* cited by examiner

*Primary Examiner*—Jurie Yun
(74) *Attorney, Agent, or Firm*—Townsend and Townsend and Crew LLP

(57) ABSTRACT

Methods for developing and using treatment plans with improved modulation for radiation therapy are disclosed. The methods involve adding an extra component to the patient-related objective function in order to make the optimization algorithm used to develop the treatment plan arrive at a solution with increased modulation. The extra component may take many forms. For example, the user may specify that the treatment plan favor solutions using a range of monitor units. The present invention is particularly useful in conjunction with radiotherapy systems having multileaf collimators for beam shaping, and in connection with advanced radiotherapy techniques, such as IMRT and arc therapy.

18 Claims, 1 Drawing Sheet

METHOD FOR CONTROLLING MODULATION STRENGTH IN RADIATION THERAPY

FIELD OF THE INVENTION

The present invention relates to treatment planning for radiation therapy, and is particularly related to use in radiation therapy systems using multileaf collimators.

BACKGROUND OF THE INVENTION

In general, radiation therapy or radiotherapy, uses a beam of ionizing radiation to treat living tissue, usually tumors. As used herein, the term radiotherapy should be broadly construed and is intended to include various techniques used to irradiate a patient, including use of photons (such as high energy x-rays and gamma rays), particles (such as electron and proton beams), and radiosurgical techniques. For purposes of the present invention, the processes of treatment planning and administering the radiation to a patient can be generalized regardless of the type of radiation used. Modern radiation therapy techniques include Intensity Modulated Radiotherapy ("IMRT"), volumetric modulated arc therapy (where the system gantry moves while radiation is delivered) and three-dimensional conformal radiotherapy ("3D conformal" or "3DCRT"). These techniques are typically implemented using a radiotherapy system, such as a linear accelerator, equipped with a multileaf collimator ("MLC"). Use of multileaf collimators in general, and IMRT in particular, allows the radiologist to treat a patient from multiple angles while varying the shape and dose of the radiation beam, thereby providing greatly enhanced ability to deliver radiation to a target within a treatment volume while avoiding excess irradiation of nearby healthy tissue. The greater freedom which IMRT and other complex radiotherapy techniques, such as afford to radiologists has made the task of developing treatment plans more difficult. While modern linear accelerators use MLCs, other methods of providing conformal radiation to a target volume are known and are within the scope of the present invention.

Treatment planning typically starts with (1) images of the treatment volume (e.g., from CT or MRI scans) and, (2) the desired dose of radiation which is to be delivered to a target, such as a tumor, within the treatment volume, and (3) the maximum dose which can be safely absorbed by tissue structures, such as organs, within the treatment volume that are adjacent to or near the tumor or other target volume. As used herein, the term "treatment volume" is used to refer to the entire volume that will be subjected to radiation, and is sometimes referred to as the "irradiated volume." The target volume, intended to receive a therapeutic prescribed dose, is sometimes referred to as the "planning target volume" ("PTV"). Thus, the target volume is within the treatment volume. Both the target volume and any nearby organs in the treatment volume may have complex three dimensional shapes adding to the difficulty of preparing a treatment plan.

The foregoing patient-specific information (e.g., volume boundaries, desired dose, etc.) is used to define or determine an objective function (sometimes referred to as a "cost function") that is then used in the treatment planning process. Thus, the typical objective function incorporates patient specific information comprising a combination of empirical data and prescribed dose information and limitations. The objective function contains what are referred to as dose volume histogram ("DVH") constraints. The DVH constraints define both how much radiation is required in the various portions of the target volume, as well as limits on radiation in the remaining portions of the treatment volume outside the target volume. For example, a DVH constraint may specify that a certain structure not receive more than A dose in B % of the structure's volume; or it may specify that a tumor should receive at least x dose in y % of the tumor volume. There may be multiple DVH constraints.

A variety of optimization algorithms have been developed to use the objective function to solve the "inverse problem" of devising and optimizing a specific, three-dimensional treatment plan for irradiating the treatment volume from a variety of angles (or, in arc therapy, while the system gantry is moving), in order to deliver a desired radiation dose to the target while minimizing irradiation of nearby tissue. The treatment plan also takes into account the capabilities and physical limitations of the radiotherapy system to be used. Generally speaking, the inverse problem involves optimizing the selection of angles, the selection of MLC leaf movements and the durations of irradiations in accordance with the constraints of the objective function. Because of the large number of variables involved and complex matrix manipulations that are required, the optimization algorithms for calculating treatment plans require substantial computational time even when using modern high speed computers.

Generally two types of algorithms are used in treatment planning: (1) dose calculations algorithms based on a given set system parameters, e.g., gantry angle, MLC leaf positions, etc., and (2) search algorithms which use various techniques to adjust system parameters between dose calculations to achieve optimization of the plan. Some exemplary dose calculation algorithms include various Monte Carlo ("MC") techniques and pencil beam convolution ("PBC"). Some exemplary search algorithms include various stochastic and deterministic methods, including various simulated annealing ("SA") techniques, algebraic inverse treatment planning ("AITP"), and simultaneous iterative inverse treatment planning ("SIITP"). Such techniques, and others, are well known in the art, and each of the techniques has advantages and disadvantages relative to the others. Each of the methods requires iterative dose calculations for optimization, and generally a high number of dose calculation iterations or "passes" are required to converge on an optimal plan. Typically, each iteration involves changing the boundary conditions using the search algorithm and recalculating the dose distribution. While a fully optimized plan might be achieved using known methods if adequate time is available, as a practical matter time constraints often limit the ability to achieve this goal.

It is noted that a treatment plan is typically implemented over a time period. Thus, the patient typically is given multiple treatments over the course of days or weeks, such that the dose delivered to the treatment volume is fractionated. During the time between treatments changes may occur in the treatment volume, for example, the tumor being irradiated may shrink in size or surrounding organs may change position. Any such changes may necessitate revising and re-optimizing the treatment plan before the next fractionated dose or "fraction" is delivered. The problem of re-optimizing a treatment plan is known, and presents somewhat different issues than achieving an initially optimized plan as described herein. Since the use of fractions does not otherwise affect the treatment planning process, it is not necessary to discuss it in further detail.

Treatment planning algorithms may be implemented as part of an overall, integrated treatment planning software package which provides additional features and capabilities. For example, a dose calculation algorithm and search algorithm may be used to optimize a set of fluence maps at each gantry angle, with a separate leaf sequencer used to calculate the leaf movements needed to deliver them. Alternatively, a dose calculation algorithm and search algorithm may be used to directly optimize leaf movements and other machine parameters. The Eclipse™ Treatment Planning System offered by the assignee of the present invention includes such an integrated software program.

BRIEF SUMMARY OF THE INVENTION

Broadly, the present invention is directed to a method of developing a treatment plan for radiotherapy using a radiotherapy system capable of beam shaping, wherein the planner determines an objective function comprising patient information including dose distribution information, the objective function is then modified by adding an extra component, selected to increase the dose modulation of said treatment plan, and then processing the modified objection function using an optimization algorithm to produce a treatment plan, such that dose modulation is improved. The extra component can take various forms. Simply, it can be is a multiplier. The extra component can include a user defined minimum, a user defined maximum or both a user defined minimum and a user defined maximum, i.e., a range. The extra component can be modified over time while the optimization algorithm operates. Likewise, the extra component can be selected based on the capabilities of the specific radiotherapy system. In such a case, the optimization algorithm may use machine parameters associated with said radiotherapy system. The dose distribution information may comprise a dose volume histogram.

The optimization algorithm may use simulated annealing or gradient back projection.

The extra component may be selected to increase the number of monitor units used in the treatment plan, or to increase the fraction of radiation that is blocked by the beam shaping structure of the radiotherapy system, or to decrease the average size of the openings of the beam shaping structure of the radiotherapy system.

In another aspect the present invention is directed to a method of treating a patient using a radiotherapy system, including developing a treatment plan for irradiating a treatment volume within the patient, wherein the step of developing a treatment plan comprises determining an objective function including patient information including dose distribution information, modifying the objective function by adding an extra component, said additional extra component being selected to increase the dose modulation of said treatment plan, and processing said modified objection function using an optimization algorithm to produce a treatment plan, and then irradiating the patient with at least a fractional dose of radiation substantially in accordance with said treatment plan. The radiation beam can be either x-rays, electrons, or protons.

DETAILED DESCRIPTION OF THE INVENTION

Figure 1:
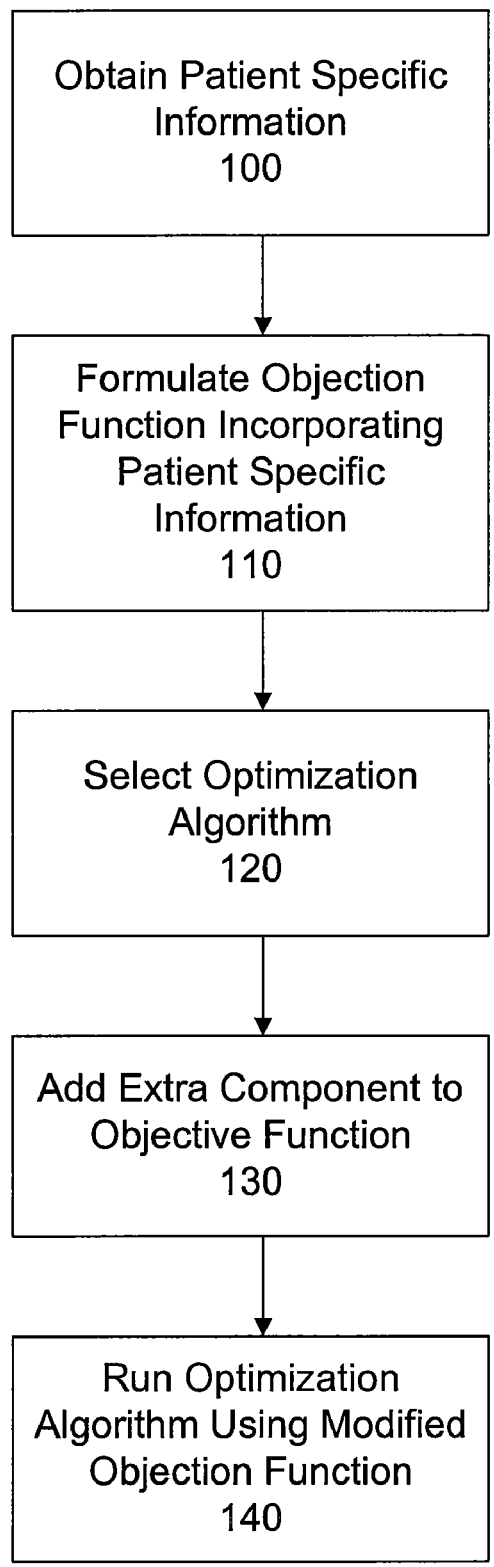
FIG. 1 is a flow chart of a method in accordance with the present invention.

As described above, treatment planning for radiotherapy seeks to inform the radiologist or other operator of the radiotherapy system how to deliver a prescribed fractional dose of radiation to a target volume, such as a tumor, while minimizing the radiation dose to surrounding tissue in the treatment volume, taking into account the capabilities of the radiotherapy system such as beam strength, beam energy, etc. Moreover, modern radiotherapy systems use sophisticated beam shaping structures, typically multileaf collimators ("MLCs"), to precisely control the shape of the radiation beam from any selected angle, and that can also be used to vary the beam strength using IMRT. Arc therapy, one of the newest techniques for radiotherapy, involves moving the gantry while delivering radiation. Sophisticated treatment planning software can interface directly with the radiotherapy system, generating machine language instructions for implementing the treatment plan. For example, such treatment planning software will calculate and generate machine control signals for the leaves of the system MLC and gantry movements.

A goal of the present invention is to increase the modulation of the treatment plan. As used herein the term modulation refers to the amount of radiation shaping that is performed on the radiation beam generated by the radiotherapy system. Thus, if the final dose delivered to the treatment volume is produced from smaller components of a radiation beam, it is more modulated. Generally, increased modulation is associated with better dose distribution in the treatment volume. Specifically, increased modulation generally allows better protection of healthy tissue in the treatment volume and also allows better dose distribution in the target volume.

Because of the complexity of the problem, treatment planning typically uses an optimization algorithm to converge on a final plan based on an objective function which comprises patient information including, for example, dose volume histogram (DVH) information and constraints. The objective function also comprises information about the capabilities of the radiotherapy system that will be used to administer the treatment plan. Usually, the objective function describes how close the plan is to the desired dose distribution, taking into account the DVH information and constraints.

Heretofore, treatment planning has either generally sought to minimize the number of monitor units ("MUs") used in the plan, (i.e., a goal has been to use as little radiation as possible), or has no considered the number of MUs as a factor. Accordingly, heretofore minimizing the number of monitor units has been part of the objective function if it was considered at all.

Treatment planning optimization algorithms can get caught in a local minimum—a point at which a non-optimal plan appears to be optimal because small parameter changes do not cause any improvement. For example, in an arc therapy plan that is being optimized using a simulated annealing approach, there may be a configuration which has an MLC sequence which conforms to the target. This MLC sequence may either be an initial configuration or may be arrived at an intermediate stage of optimization. Near this conformal solution in optimization space may be a solution with a low number of MUs, relatively good target volume coverage, and relatively good critical organ sparing. In such a case, the optimizer can easily get stuck at this solution even where there are better solutions with more modulation.

In some instances, known techniques for breaking out of local minima will allow the optimization algorithm in use to arrive at a better solution. For example, a "temperature" variable is generally used with simulated annealing to avoid the local minima problem. It is known to decrease the temperature to zero as optimization converges on a solution. Thus, the ability of temperature overcome this problem depends on the temperature value when the local minima is reached. Moreover, even when techniques for breaking out of local minima work, they can be time consuming. Since only a limited amount of time is available to the optimization software to arrive at a treatment plan, any time spent breaking out of a local minimum can adversely affect the quality of the final plan.

The present invention addresses this problem by modifying the objective function to promote treatment plan solutions which provide greater modulation. Specifically, the present invention involves adding an extra component to the objective function for this purpose, i.e., to avoid a local minimum or to quickly guide the optimization algorithm from a local minimum with low modulation to a better solution with higher modulation. The extra component can take a variety of different forms as described herein.

While simulated annealing has been used in the above example, the problem identified by the inventors and its solution apply to other optimization techniques, such as those identified in the Background section, above. For example, while simulated annealing is often used with direct aperture models (i.e., models that use machine parameters), gradient back projection is often used with fluence based models. While other approaches are sometimes used, these two combinations, direct aperture/simulated annealing and fluence/back projection are the two most common optimization methods. Modification of the objective function by adding a component in accordance with the present invention works with both of them.

In one implementation of the present invention, the extra component favors increasing the number of MUs. It will be appreciated that there is a direct correlation between modulation and the number of monitor units used for treatment. Selecting a treatment plan that uses more MUs to obtain the same level of radiation of the treatment volume means that, on average, more of the beam is being blocked. This, in turn, means that beam modulation has increased. Thus, the extra component may simply be requiring a minimum number of MUs. Likewise, the extra component may be a factor that favors solutions where the MUs are in a specific range, for example between 500-800 MUs. The selected number or range can be based on empirical knowledge about the clinical case and/or the radiotherapy system being used. For example, the range 500-800 MUs may be associated with a particular type of system, e.g., Varian Clinac® brand systems. Moreover, rather than merely favoring a range, minimum and maximum MU amounts can be specified.

Other techniques are available to increase modulation, and can be used to modify the objective function. One such technique is to directly favor solutions which provide increased modulation. Another technique is to add an extra component to favor a range of MLC openings.

As an example, DVH constraints may specify that a certain structure should receive at least A Gy dose in B % of the structure within the target volume, while another structure outside the target volume should not receive more than X Gy dose in Y % of the structure. For one DVH constraint the objective function can be, for example, the fraction of elements violating the constraint times the sum of squared deviations from constraint dose for each point violating the constraint.

Often there are multiple DVH constraints which may be summed. In this situation the objective function would be T=M×D, where D is the sum of the DVH constraints and M is the extra component in the form of a modulation multiplier. In an implementation of the present invention which comprises favoring a range of MUs, let $D_{MIN}$ be the lower end of the range and let $D_{MAX}$ be the upper end. (As noted the range may be user-defined.) The value of M can be set as follows: (1) M=1 for $D_{MIN}<MU<D_{MAX}$; (2) $M=S\char`^((D_{MIN}-MU)/D_{MIN})$ for $MU<D_{MIN}$; and (3) $S\char`^((MU-D_{MAX})/D_{MAX})$ for $MU>D_{MAX}$; where S is the strength of the modulation effect in the objective function and MU is the number of monitor units. It can be seen that this favors optimization in the specified range. Note that in accordance with the present invention, the value of S may be reduced as optimization proceeds.

FIG. 1 is a flow chart of an embodiment of the present invention. Starting at step 100, patient specific information is first collected. This information may include information about the target volume (e.g., tumor), the prescribed dose of radiation to be administered to the target volume, neighboring tissue information, limits on the amount of radiation that may be absorbed by the neighboring tissue, etc. Thus, the patient information includes DVH constraint information. Next, at step 110, an initial objective function is formulated based at least in part on the patient information from step 100. At step 120, at least one optimization algorithm is selected for developing the treatment plan. While step 120 is shown as following steps 100 and 110, it can be selected before or between those steps. Moreover, the optimization algorithm may be built into treatment planning software such that its selection is automatic, i.e., there is no user choice involved—it is selected by activation of the program. At step 130, the objective function is modified by adding an extra component that increases the dose modulation of the final treatment plan. Finally, at step 140 the optimization algorithm processes the objective function to develop a treatment plan.

The embodiments described above are illustrative of the present invention and are not intended to limit the scope of the invention to the particular embodiments described. Accordingly, while one or more embodiments of the invention have been illustrated and described, it will be appreciated that various changes can be made therein without departing from the spirit or essential characteristics thereof. Accordingly, the disclosures and descriptions herein are not intended to be limiting of the scope of the invention, which is set forth in the following claims.

What is claimed is:

1. A method of developing a treatment plan for radiotherapy using a radiotherapy system having a beam shaping structure, comprising,
   determining an objective function comprising patient information including dose distribution information,
   modifying the objective function by adding an extra component, said extra component being selected to increase the dose modulation of said treatment plan,
   processing said modified objective function using an optimization algorithm to produce a treatment plan.

2. The method of claim 1 wherein said extra component is a multiplier.

3. The method of claim 1 wherein said extra component comprises a user defined minimum.

4. The method of claim 1 wherein said extra component comprises a user defined maximum.

5. The method of claim 1 wherein said extra component comprises both a user defined minimum and a user defined maximum.

6. The method of claim 1 wherein said extra component is modified over time.

7. The method of claim 1 wherein said treatment plan is developed for a specific radiotherapy system and said extra component is selected based on the capabilities of said radiotherapy system.

8. The method of claim 7 wherein said optimization algorithm uses machine parameters associated with said radiotherapy system.

9. The method of claim 1 wherein said optimization algorithm comprises simulated annealing.

10. The method of claim 1 wherein said optimization algorithm comprises gradient back projection.

11. The method of claim 1 wherein said objective function comprises monitor units and said extra component tends to increase the number of monitor units used in said treatment plan.

12. The method of claim 1 wherein said extra component tends to increase the fraction of radiation that is blocked by the beam shaping structure of the radiotherapy system.

13. The method of claim 1 wherein said extra component tends to decrease the average size of the opening of the beam shaping structure of the radiotherapy system.

14. The method of claim 1 wherein said dose distribution information comprises dose volume histogram information.

15. A method of treating a patient using a radiotherapy system, comprising:

developing a treatment plan for irradiating a treatment volume within the patient, said step of developing a treatment plan comprising:

determining an objective function comprising patient information including dose distribution information, modifying the objective function by adding an extra component, said extra component being selected to increase the dose modulation of said treatment plan, and processing said modified objective function using an optimization algorithm to produce a treatment plan, and irradiating the patient with at least a fractional dose of radiation substantially in accordance with said treatment plan.

16. The method of claim 15 wherein said step of irradiating comprises use of an x-ray beam.

17. The method of claim 15 wherein said step of irradiating comprises use of an electron beam.

18. The method of claim 15 wherein said step of irradiating comprises use of a proton beam.

* * * * *